US00PP14391P29

(12) United States Plant Patent
Klemm

(10) Patent No.: US PP14,391 P2
(45) Date of Patent: Dec. 23, 2003

(54) NEW GUINEA IMPATIENS PLANT NAMED 'KLEI01028'

(50) Latin Name: *Impatiens hawkeri*
Varietal Denomination: KLEI01028

(75) Inventor: Nils Klemm, Stuttgart (DE)

(73) Assignee: Klemm & Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/259,983

(22) Filed: Sep. 29, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—A Para
(74) *Attorney, Agent, or Firm*—C. A. Whealy

(57) ABSTRACT

A new and distinct cultivar of New Guinea Impatiens plant named 'KLEI01028', characterized by its compact, mounded and outwardly spreading plant habit; freely branching growth habit; dark green-colored leaves; freely flowering habit with flowers positioned above or beyond the foliage; and large bright red-colored flowers.

1 Drawing Sheet

Botanical classification/cultivar designation: *Impatiens hawkeri* cultivar KLEI01028.

BACKGROUND OF THE INVENTION

The present Invention relates to a new and distinct cultivar of New Guinea Impatiens plant, botanically known as *Impatiens hawkeri,* and hereinafter referred to by the cultivar name KLEI01028.

The new Impatiens is a product of a planned breeding program conducted by the Inventor in Stuttgart, Germany. The objective of the breeding program is to develop new freely branching Impatiens cultivars with numerous large flowers and interesting flower and foliage colors.

The new Impatiens originated from a cross-pollination made by the Inventor during the fall of 1998 of a proprietary *Impatiens hawkeri* selection identified as code number A 069 not patented, as the female, or seed parent, with a proprietary *Impatiens hawkeri* selection identified as code number P 139, not patented, as the male, or pollen parent. The cultivar KLEI01028 was discovered and selected by the Inventor as a flowering plant within the progeny of the stated cross-pollination in controlled environment in Stuttgart, Germany, in May, 1999.

Asexual reproduction of the new cultivar by terminal cuttings taken in a controlled environment in Stuttgart, Germany, since 1999, has shown that the unique features of this new Impatiens are stable and reproduced true to type in successive generations.

SUMMARY OF THE INVENTION

The following traits have been repeatedly observed and are determined to be the unique characteristics of 'KLEI01028'. These characteristics in combination distinguish 'KLEI01028' as a new Impatiens cultivar and distinguish it from other known Impatiens cultivars:

1. Compact, mounded and outwardly spreading plant habit.
2. Freely branching growth habit.
3. Dark green-colored leaves.

4. Freely flowering habit with flowers positioned above or beyond the foliage.
5. Large bright red-colored flowers.

Plants of the new Impatiens differ primarily from plants of the parent selections in flower color as plants of the female and male parent selections have dark red and purple-colored flowers, respectively. In addition, plants of the new Impatiens have larger flowers than plants of the female parent selection.

Plants of the new Impatiens can be compared to plants of the cultivar Delhi, disclosed in U.S. Plant Pat. No. 11,694. In side-by-side comparisons conducted in Stuttgart, Germany, plants of the new Impatiens differed from plants of the cultivar Delhi in the following characteristics:

1. Plants of the new Impatiens flowered later than plants of the cultivar Delhi.
2. Flowers of plants of the new Impatiens were bright red in color whereas flowers of plants of the cultivar Delhi were more crimson red in color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'KLEI01028' grown in a container.

DETAILED BOTANICAL DESCRIPTION

The cultivar KLEI01028 has not been observed under all possible environmental conditions. The phenotype may vary somewhat with variations in environment such as temperature and light intensity without, however, any variance in genotype. The aforementioned photograph and following observations and measurements describe plants grown in Stuttgart, Germany during the spring, under commercial practice in a glass-covered greenhouse. Plants were grown in 12-cm containers for about 12 weeks after planting rooted cuttings. During the production period, day temperatures ranged from 18 to 24° C. and night temperatures ranged from 16 to 18° C. In the following description, color references are made to The Royal Horticultural Society Colour Chart, 1995 Edition, except where general terms of ordinary dictionary significance are used.

Botanical classification: *Impatiens hawkeri* cultivar KLEI01028.

Commercial classification: New Guinea Impatiens cultivar KLEI01028.

Parentage:

*Female parent.*—Proprietary *Impatiens hawkeri* selection identified as code number A 069, not patented.

*Male parent.*—Proprietary *Impatiens hawkeri* selection identified as code number P 139, not patented.

Propagation:

*Type cutting.*—Terminal cuttings.

*Time to initiate roots.*—About 10 days at 20° C.

*Time to produce a rooted cutting.*—About 21 days at 20° C.

*Root description.*—Fine to thick, fibrous; cream-white in color.

*Rooting habit.*—Freely branching, dense.

Plant description:

*General appearance.*—Compact, mounded and outwardly spreading plant habit.

*Growth and branching habit.*—Freely branching, about eight lateral branches per plant develop without pinching, that is, removal of the terminal apices. Moderately vigorous growth habit; densely foliated.

*Plant height.*—About 12.5 cm.

*Plant spread.*—About 28 cm.

*Lateral branch description.*—Length: About 7 cm. Diameter: About 7 mm. Internode length: About 3 cm. Texture: Smooth, glabrous. Color: 178B.

*Foliage description.*—Arrangement: Opposite or in whorls. Length, mature leaves: About 13 cm. Width, mature leaves: About 4.5 cm. Shape: Lanceolate, oblong. Apex: Acuminate. Base: Attenuate. Margin: Serrulate with fine ciliation. Texture, both surfaces: Smooth, glabrous, leathery. Venation pattern: Pinnate. Color: Young foliage, upper surface: 137B, glossy. Young foliage, lower surface: 138C. Fully expanded foliage, upper surface: 139A; glossy. Fully expanded foliage, lower surface: 138C. Venation, upper and lower surfaces: 185C. Petiole: Length: About 3 cm. Diameter: About 3.5 mm. Texture, upper and lower surfaces: Smooth, glabrous. Color, upper and lower surfaces: 185C.

Flower description:

*Flower type and flowering habit.*—Single, large and rounded flowers. Freely flowering, usually about five flowers and flower buds in clusters per lateral branch. Flowers positioned above and beyond the foliage and typically face upward or outward. Flowers rounded and mostly flat when fully opened. Flowers last about 10 to 14 days on the plant depending on environmental conditions. Petals self-cleaning; gynoecium persistent. Flowers not fragrant. Flowering indeterminate and continuous.

*Flowering season.*—Year-round under greenhouse conditions. In the garden, flowering from spring until fall.

*Flower length.*—About 8.2 cm.

*Flower width.*—About 7.6 cm.

*Flower depth* (*thickness*).—About 1.4 cm.

*Flower buds.*—Rate of opening: From flower bud to fully open flower, typically about five to seven days depending on temperature. Length: About 1.9 cm. Diameter: About 9 mm. Shape: Ovoid. Texture: Smooth, glabrous. Color: 53B.

*Petals.*—Quantity: Five per flower, imbricate. Length: Banner petal: About 4.1 cm. Lateral petals: About 4.1 cm. Lower petals: About 4.6 cm. Width: Banner petal: About 5.5 cm. Lateral petals: About 4.1 cm. Lower petals: About 4.3 cm. Shape: Roughly cordate. Apex: Emarginate. Base: Rounded to acute. Margin: Entire. Texture: Smooth; satiny. Color: When opening and fully opened, upper surface: 45B; color does not fade with development. When opening and fully opened, lower surface: 46D.

*Spur.*—Length: About 6.4 cm. Diameter: At flower: About 2.5 mm. At apex: About 0.7 mm. Texture: Smooth, glabrous. Color: 185B.

*Peduncles.*—Length: About 6.5 cm. Diameter: About 2.2 mm. Strength: Strong, flexible. Aspect: About 45° from the stem. Texture: Smooth, glabrous. Color: 174D.

*Reproductive organs.*—Androecium: Stamen number: Five fused at anthers, filaments free, hooded. Anther shape: Obovate. Anther length: About 6.5 mm. Anther width: About 4.5 mm. Anther height: About 1.5 mm. Anther color: Creamy white, close to 157A. Amount of pollen: Abundant. Pollen color: Creamy white, close to 157A. Gynoecium: Pistil number: One. Pistil length: About 6 mm. Stigma shape: Columnar, five-segmented. Stigma color: Creamy white, close to 157A. Style color: Creamy white, close to 157A. Ovary color: 141C.

*Fruit/seed development.*—Fruit and seed development has not been observed.

Disease/pest resistance: Plants of the new Impatiens have not been observed to be resistant to pathogens or pests common to Impatiens.

Weather tolerance: In Stuttgart, Germany, plants of the new Impatiens have been observed to be relatively tolerant to wind and rain and to tolerate temperatures from 12 to 30° C.

It is claimed:

1. A new and distinct cultivar of New Guinea Impatiens plant named 'KLEI01028', as illustrated and described.

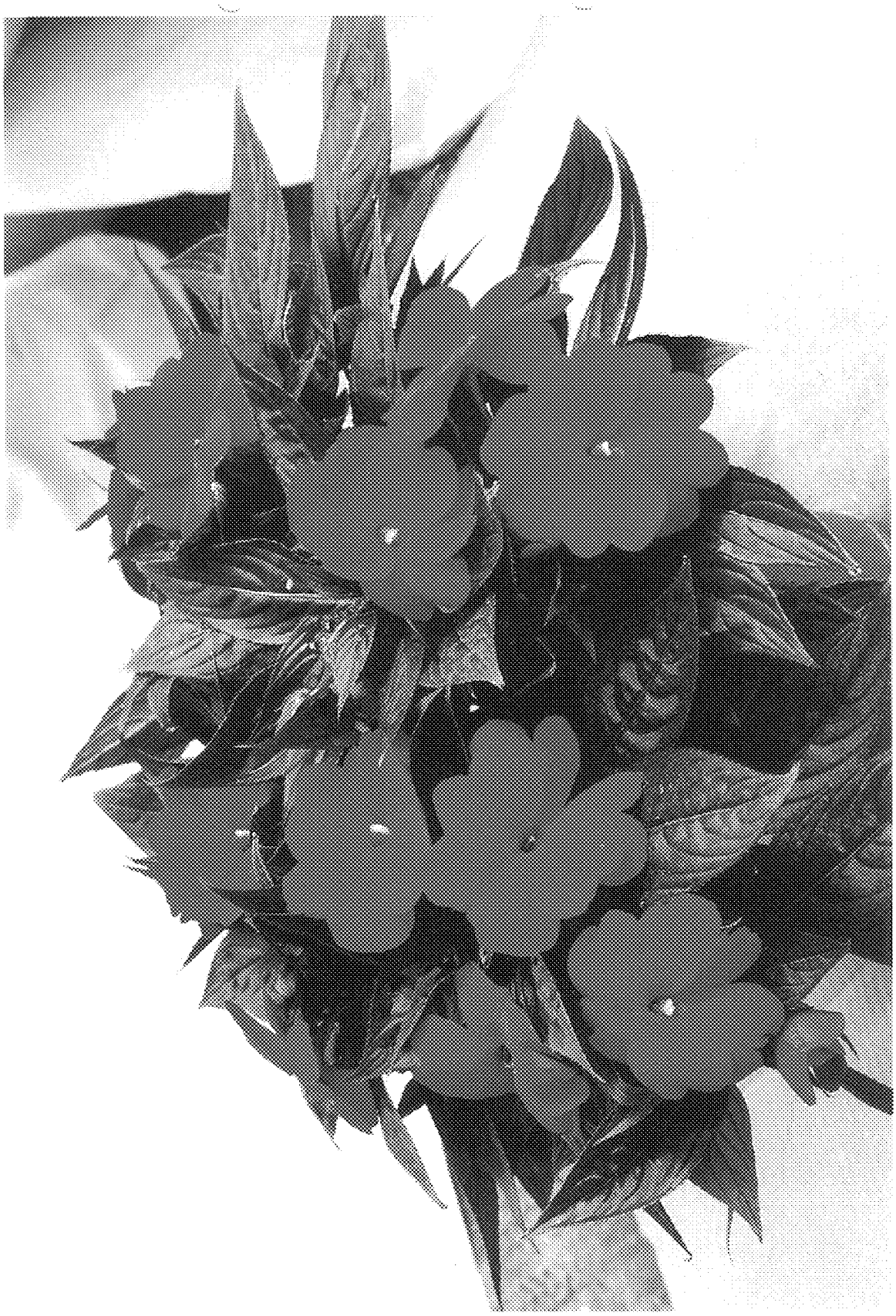

* * * * *